United States Patent [19]

Yerushalmi

[11] Patent Number: 4,601,296
[45] Date of Patent: Jul. 22, 1986

[54] HYPERTHERMIA APPARATUS

[75] Inventor: Aharon Yerushalmi, Rehovot, Israel

[73] Assignee: Yeda Research and Development Co., Ltd., Rehovot, Israel

[21] Appl. No.: 540,016

[22] Filed: Oct. 7, 1983

[51] Int. Cl.$^4$ ............................................. A61N 5/02
[52] U.S. Cl. ..................................... 128/804; 128/401
[58] Field of Search ............... 128/804, 784, 786, 788, 128/400, 401, 303.1, 736

[56] References Cited

U.S. PATENT DOCUMENTS

| | | | |
|---|---|---|---|
| 3,228,400 | 1/1966 | Armao | 128/401 X |
| 4,375,220 | 3/1983 | Matvias | 128/804 |

FOREIGN PATENT DOCUMENTS

| | | | |
|---|---|---|---|
| 2407559 | 8/1975 | Fed. Rep. of Germany | 128/804 |
| 81/03616 | 12/1981 | PCT Int'l Appl. | 128/401 |

OTHER PUBLICATIONS

Giovanella et al, "Selective Lethal Effect . . . Cells", Cancer Research, vol. 36, pp. 3944–3950, 1976.
Manning et al, "Clinical Hyperthermia . . . " Cancer, vol. 49, pp. 205–216, 1982.
Overgaard, "Fractionated Radiation . . . ", Cancer, vol. 48, pp. 1116–1123, 1981.
Gerner, "Influence of Growth State . . . " Cancer Research, vol. 39, 981–986, 1979.
Marmor et al, "Combined Radiation . . . ", Cancer, vol. 46, No. 9, pp. 1986–1991, 1980.
Yerushalmi, "Combined Treatment . . . " Br. J. Cancer, 37, 827, 1978.
Yerushalmi et al, "Local Hyperthermia . . . ", Prostate, 3, 623–630, 1982.
Buck, "Slotted Cylinder Antenna . . . ", Conf., Proc. 8th Eur. Mic. Conf., Paris, France, Sep. 4–8, 1978, pp. 548–552.
Mendecki, "Microwave Applicators . . . ", Int. J. Rad. Onc. Biol. Phys., vol. 6, No. 11, pp. 1583–1588, Nov. 1980.

*Primary Examiner*—Lee S. Cohen
*Attorney, Agent, or Firm*—Browdy and Neimark

[57] ABSTRACT

Apparatus for hyperthermic treatment of tumors comprising a probe insertable into a body cavity in the vicinity of a tumor to be treated, the probe including a radiation emitting antenna and a conduit system for the passage of a cooling fluid adjacent the outer surface thereof for cooling of tissue lying adjacent the probe.

8 Claims, 10 Drawing Figures

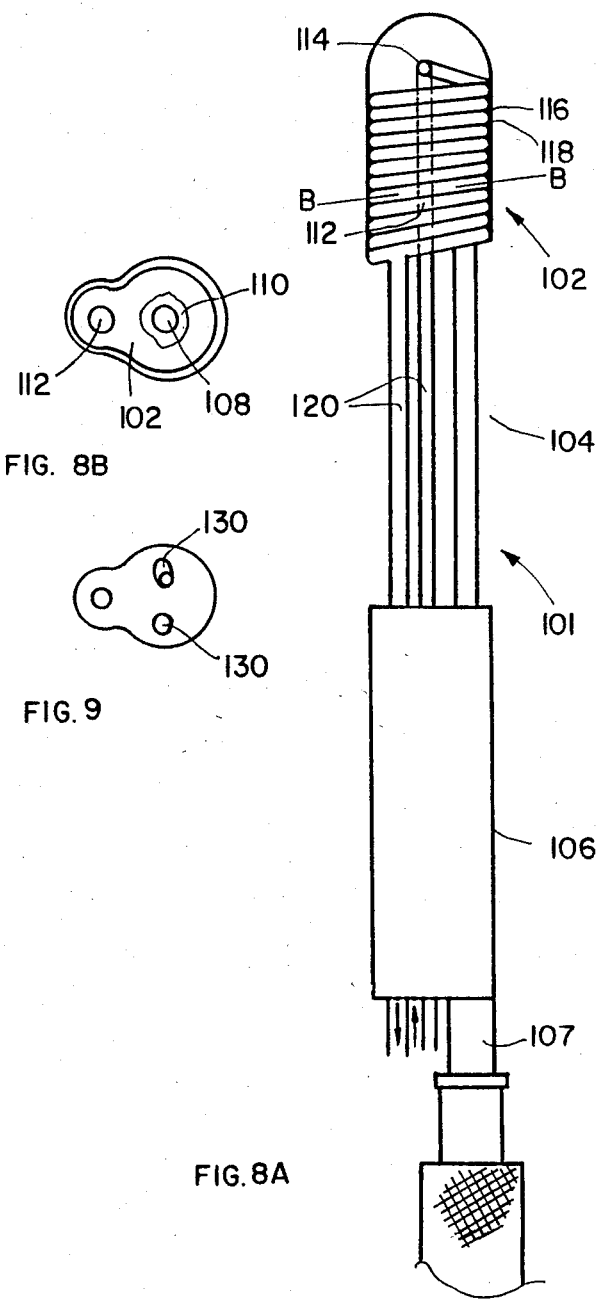

HYPERTHERMIA APPARATUS

FIELD OF THE INVENTION

The present invention relates to hyperthermia generally and more particularly to a technique and apparatus for hyperthermic treatment of tumors of the prostate and elsewhere in the lower body.

BACKGROUND OF THE INVENTION

The use of hyperthermia in treatment of malignant tumors is well known and is documented in a large number of scientific reports. Recent summary reports which reflect the activity in this field appear in:

1. Manning, M. R.; Cetas, T. C.; Miller R. C.; Oleson, J. R.; Connort, W. G.; Gerner, E. W., Clinical Hyperthermia; Results of a Phase I Trail Employing Hyperthermia Alone or in Combination with External Beam or Interstitial Radiotherapy. Cancer Vol 49, pp 205–216, 1982.

2. Overgaard, J. Fractionated Radiation and Hyperthermia. Cancer, Vol 48, pp. 1116–1123, 1981.

A brief summary of the research carried out by the present applicants appears in a preprint entitled:

3. Yerushalmi, A.; Servadio, C.; Fishelovitz, Y.; Leib, Z.; Rankowsky, A.; Stein J. A.; Local Hyperthermia for Treatment of the Prostate: A Preliminary Report. Prostate, 3; 623–630, 1982.

It has been appreciated by applicants that a major limitation to the successful application of hyperthermia has been the undesired heating of healthy tissue in the vicinity of the tumor. Efforts have been made to solve this problem for superficial tumors. See Marmor J. B.; Hahn, G. M.; Combined Radiation and Hyperthermia in Superficial Tumors. Cancer Vol 46, pp 1986–1991, 1980.

Apparatus for hyperthermic treatment including a probe member which is adapted to be inserted into a body cavity, wherein the probe includes an RF microwave antenna and means for circulating a cooling fluid through the probe, is known as are devices for monitoring the temperature adjacent the probe and at the heating target location for controlling the operation of the antenna and cooling mechanisms. References showing such apparatus appear in U.S. Pat. Nos. 2,074,634, 4,237,898, 4,140,130 and 4,290,435.

SUMMARY OF THE INVENTION

The present invention seeks to provide a technique and apparatus for hyperthermic treatment of tumors which seek to overcome the well known problems of undesired heating of tissue.

There is thus provided in accordance with an embodiment of the present invention apparatus for hyperthermic treatment of tumors comprising a probe insertable into a body cavity in the vicinity of a tumor to be treated, the probe including a radiation emitting antenna and a conduit system for the passage of a cooling fluid adjacent the outer surface thereof for cooling of tissue lying adjacent the probe.

Further in accordance with a preferred embodiment of the invention, the conduit system comprises a coiled fluid circulation conduit arranged peripherally of the probe.

Additionally in accordance with a preferred embodiment of the present invention, the coiled fluid circulation conduit effectively surrounds a major part of the peripheral surface of the probe adjacent the antenna.

Further in accordance with an embodiment of the invention the coiled fluid circulation conduit defines a ribbed outer surface engaging the surrounding body tissue, providing increased cooling surface area as compared with the peripheral probe surface and enhanced resistance to inintended displacement of the probe in the body cavity.

Additionally in accordance with a preferred embodiment of the present invention, the probe comprises a forward antenna containing portion which is provided with the peripherally disposed fluid circulation conduit and a rearward support portion, the rearward portion being arranged to be of significantly less cross-sectional area than the forward portion whereby the probe is arranged such that the rearward portion is engageable by the sphincter muscles of a patient, thus retaining the forward antenna containing portion in precise desired position.

Further in accordance with a preferred embodiment of the present invention, the probe also include temperature sensing apparatus for indicating the temperature at the surface of the probe.

Additionally in accordance with a preferred embodiment of the invention, the apparatus also includes automatic temperature responsive control apparatus which is operative to control the operation of the antenna in response thereto and to terminate operation of the antenna in response to potential overheating of adjacent tissue.

Further in accordance with an embodiment of the invention, the antenna comprises a plurality of antennas producing an overall directional radiation pattern.

Additionally in accordance with an embodiment of the present invention the probe comprises an integrally formed probe housing having cavities formed therein wherein are disposed the antenna and a part of the cooling conduit system. Alternatively, the cooling conduit system may be disposed entirely outside of the probe housing.

Further in accordance with an embodiment of the present invention there is provided a technique for hyperthermic treatment of tumors comprising the steps of inserting a probe including an antenna and external cooling means into a body cavity adjacent the tumor, operating the probe to provide simultaneous radiation and direct cooling of tissue adjacent the probe, sensing the temperature at the surface of the probe and interactively controlling the provision of the radiation as a function of the sensed temperature in order to prevent accidental overheating of the adjacent tissue.

BRIEF DESCRIPTION OF THE DRAWING

The present invention will be understood and appreciated more fully from the following detailed description taken in conjunction with the drawings in which:

FIG. 8A is a side view illustration of a preferred embodiment of a probe assembly;

FIG. 8B is a cross sectional view of the forward section of FIG. 8A; and

FIG. 9 is a cross sectional view of an alternative probe configuration.

DETAILED DESCRIPTION OF THE INVENTION

Figure 1:
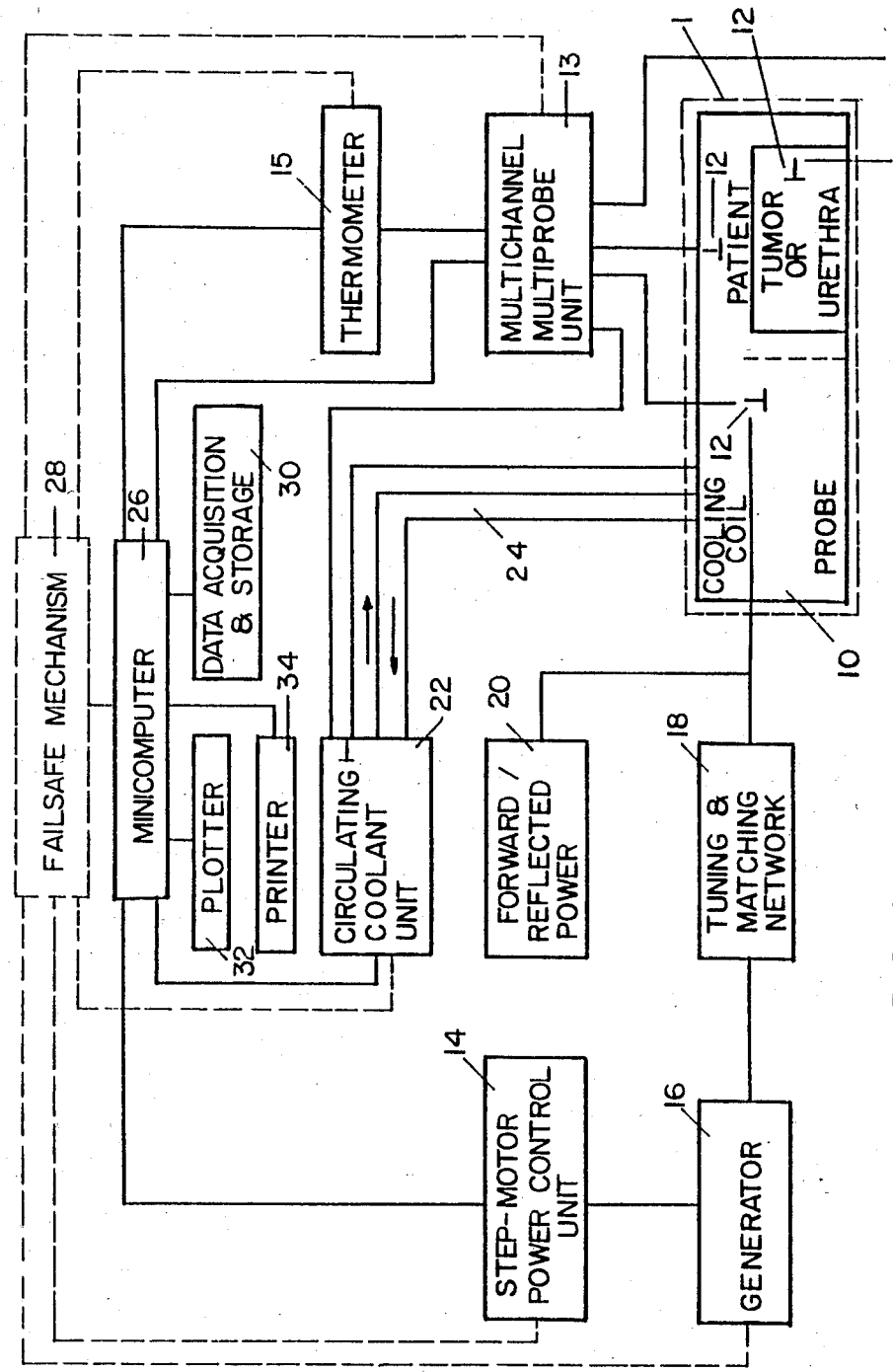
FIG. 1 is a generalized block diagram illustration of hyperthermic treatment apparatus constructed and operative in accordance with a preferred embodiment of the present invention.

Reference is now made to FIG. 1 which illustrates apparatus for hyperthermic treatment of tumors constructed and operative in accordance with a preferred embodiment of the present invention. Throughout the specification and claims, the term "tumor" will be used in a general sense to means both benign and malignant tumors. The apparatus is based on a probe 10, illustrated in exemplary form in FIG. 3, and which includes radiation emitting antenna means and cooling fluid conduit means. Temperature sensing means 12 may also be incorporated in one or more of the fluid conduit means. Additionally, temperature sensing means 12, such as a thermocouple or another substantially non-perturbing temperature sensor may be disposed on the outer surface of the probe and enclosed together with the probe in a suitable protective sheath. An additional temperature sensor 12 is provided interiorly or adjacent to the tumor sought to be treated.

Probe 10 is designed to be readily easily insertable into a body cavity, such as the rectal cavity, preferably without requiring sedation of the patient undergoing treatment. Temperature sensors 12 are connected via a multichannel multiprobe unit 13 that provides time shared scanning of sensors 12 to a thermometer 15, which provides an output indication of the measured temperatures at the various sensors.

A radiation generating unit is provided and includes a step-motor controlled power control unit 14 such as a standard unit manufactured by Hewlett Packard of the U.S.A., a radiation generator 16, typically a microwave generator such as a CMD 12 manufactured by Raytheon of the U.S.A., a tuning and matching network 18 according to the frequency and impedance used, such as a conventional unit manufactured by Omnispectra of the U.S.A., a Forward/Reflected Power Meter 20, such as a unit manufactured by Hewlett Packard and one or more antennas such as an antenna manufactured by RCA Inc. of the U.S.A. incorporated within probe 10.

A coolant circulation unit 22 is maintained in fluid communication with fluid conduit means within probe 10 by means of a pair of flexible conduits 24.

A minicomputer 26, such as a HP 9825B, controls the overall operation of the apparatus and provides control signals to the power control unit 14, and the circulation unit 22, while receiving status inputs from thermometer 15 and from probe 10. Failsafe logic circuitry 28 provides automatic termination of radiation in the event of a malfunction in any of the major operating systems, including the power control unit 14, the generator 16, the temperature sensing means 12 or the probe 10. Failsafe circuitry 28 is also operative to provide immediate termination of radiation in the event of sensed overheating at temperature sensing means 12.

Also communicating with minicomputer 26 are various recording devices and memory devices for maintenance of records. These may include conventional data acquisition and storage means 30, a plotter 32 and a printer 34.

It is noted in general that producing intratumor temperatures above 41 degrees centigrade is selectively lethal to radiation resistant cells, (See Giovanella, B. C.; Stehlin, J. S.; Morgan, A. C.; Selective Lethal effect of Supranormal Temperatures on Human Neoplastic Cells, *Cancer Research* Vol 36, pp 3944–3950, 1976.), and hypoxic cells (See Gerner E. W.; Holmes, P. W.; McCullough, J. A., Influence of Growth State on Several Thermal Responses of EMT6/A7 Tumor Cells in vitro. *Cancer Research* Vol 39, 981–986, 1979.) Synergism of hyperthermia with radiation and drug therapy is described in the following references: Yerushalmi, A.; Treatment of a Solid Tumor by Local Hyperthermia and Ionizing Radiation; Dependence on Temperature and Dose, *European J. Cancer* Vol 12, pp 807–812, 1976 and Yerushalmi, A., Combined Treatment of a Solid Tumor by Local Hyperthermia and Actinomycin-D.*Br. J. Cancer* Vol 37, pp 827–832, 1978.

In the treatment of a prostate tumor, the temperature adjacent the tumor is measured typically by means of a thermocouple inserted into the urethra by means of a Foley catheter. Alternatively or additionally, a thermocouple may be inserted into the tumor by surgery or via a needle. It is noted on the basis of clinical experience of the applicants that intraprostatic temperatures correspond to temperature measurements taken in the prostatic urethra. (See Ref (3) above.)

The operation of the apparatus of FIG. 1 will now be described briefly. Initially the predetermined temperature to be achieved at the tumor during treatment and maximum permissible tissure temperatures are selected by the operator.

The principle of operation of the apparatus of FIG. 1 is that the output energy of the microwave generator is increased in a stepwise fashion on the basis of frequent temperature measurements at, or in the vicinity of, the tumor. If between measurement samples, the temperature at the tumor is seen to rise, the output energy is not increased. In such a case, the output energy is maintained at the same level while the temperature is repeatedly sampled until the temperature is found not to increase between samples.

Fail safe operation is provided by sensing the temperature in the cooling fluid and also at the tissue location adjacent the probe along the radiation pathway from the antenna to the tumor. The temperature thus sensed is representative of the maximum possible temperature produced in the normal tissue adjacent the probe.

Figure 2:
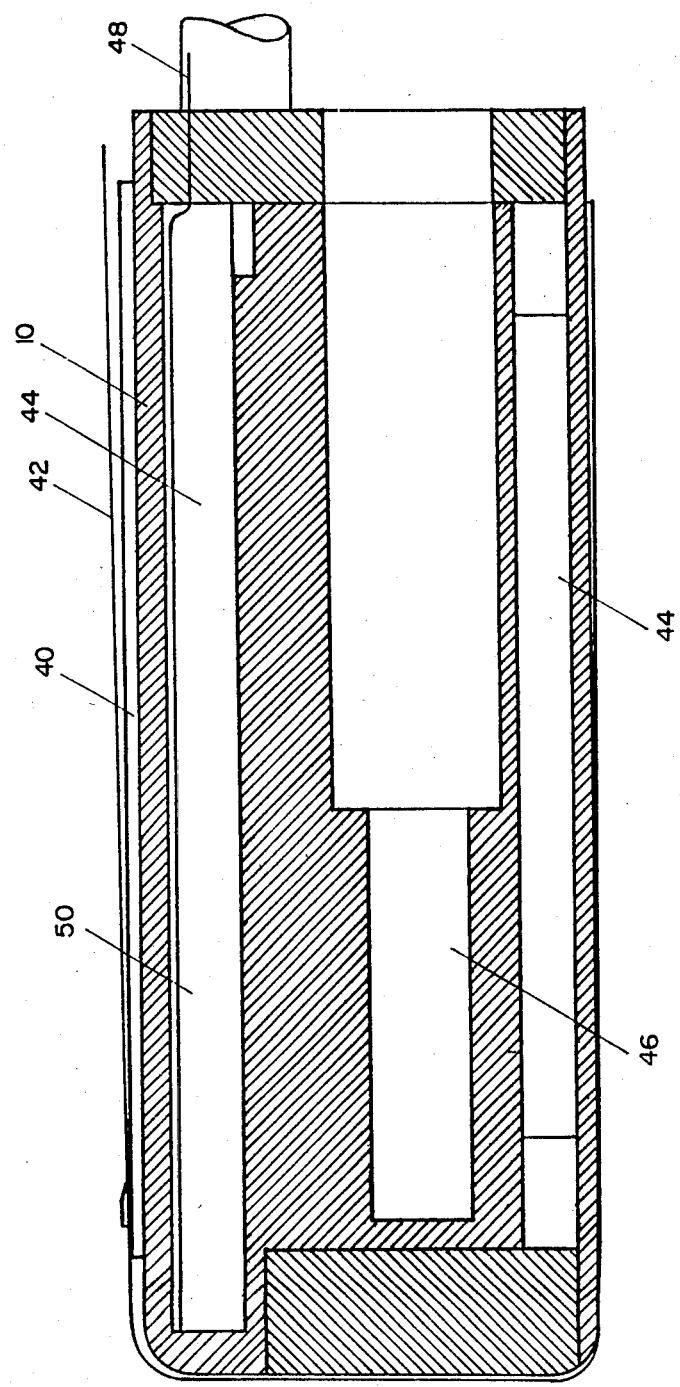
FIG. 2 is a pictorial illustration of a probe useful in accordance with the present invention.
Figure 3:
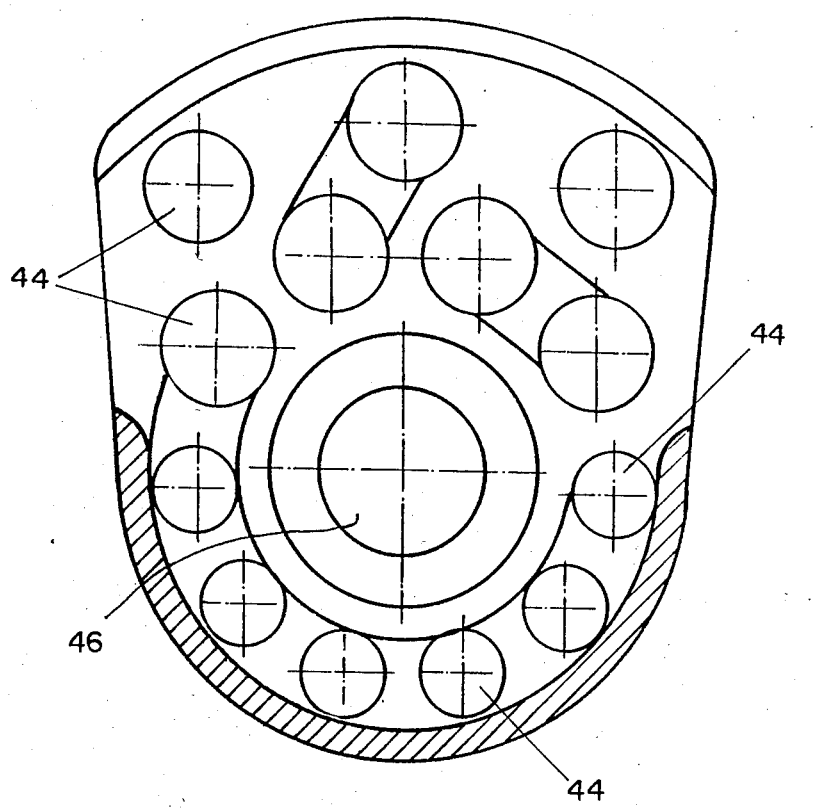
FIGS. 3, 4, 5, and 6 are each cross sectional illustrations of probes in accordance with four respective alternative embodiments of the present invention.

Reference is now made to FIGS. 2 and 3 which are sectional illustrations of a probe 10 useful in accordance with a preferred embodiment of the present invention. The probe body is typically formed of Teflon. In order to be insertable into the rectal cavity of a patient, the maximum cross sectional dimension of the probe is preferably 25 mm. According to a preferred embodiment of the invention, a thermocouple 40 is disposed along the outer surface of probe 10 and is enclosed together therewith by means of an outer sheath 42. It is noted that probe 10 is provided with a plurality of cooling fluid circulation conduits 44 which surround an antenna 46, such as a quarter wavelength microwave antenna. Conduits 44 are coupled to a pair of connectors 48 for coupling via flexible conduits, not shown, to circulating coolant unit 22 (FIG. 1). A temperature sensor 50, such as a thermocouple, is located within one of conduits 44 and is coupled via suitable electrical coupling means (not shown) to multiprobe unit 13 (FIG. 1).

It is a particular feature of the configuration of FIGS. 2 and 3, that cooling conduits are provided to entirely surround antenna 46. It is appreciated that a similar type of configuration may be applied to the alternative probe configurations shown in FIGS. 4–6 described hereinafter.

A number of alternative probe configurations may be provided for probe 10, in order to conform to different tumor shapes and configurations and different body configurations of the patient.

Figure 4:
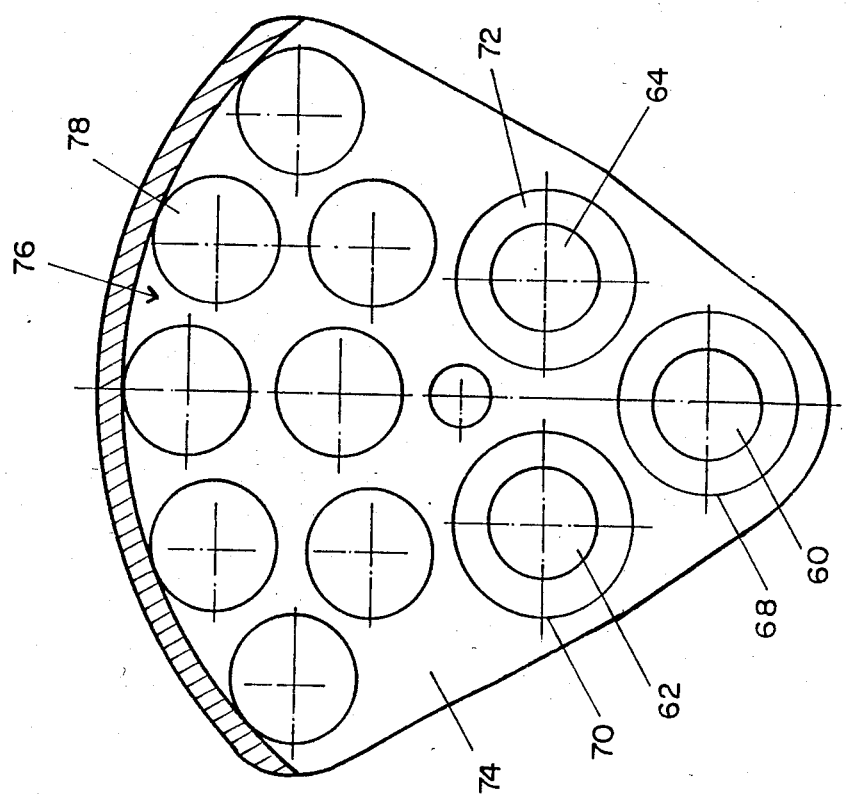

Reference is now made to FIG. 4 which illustrates a generally triangular circular segment shaped cross sectional configuration of probe 10. Here three antennas 60, 62 and 64 are arranged in respective bores 68, 70 and 72 in a housing 74 so as to provide a selectable directional output. In the embodiment of FIG. 4 one or more of the antennas may be operated at desired relative output intensities to provide the desired output direction and intensity suitable for the shape and location of the tumor. A cooling conduit system 76 is provided at the broader portion of the housing and includes a plurality of interconnected conduits 78.

Figure 5:
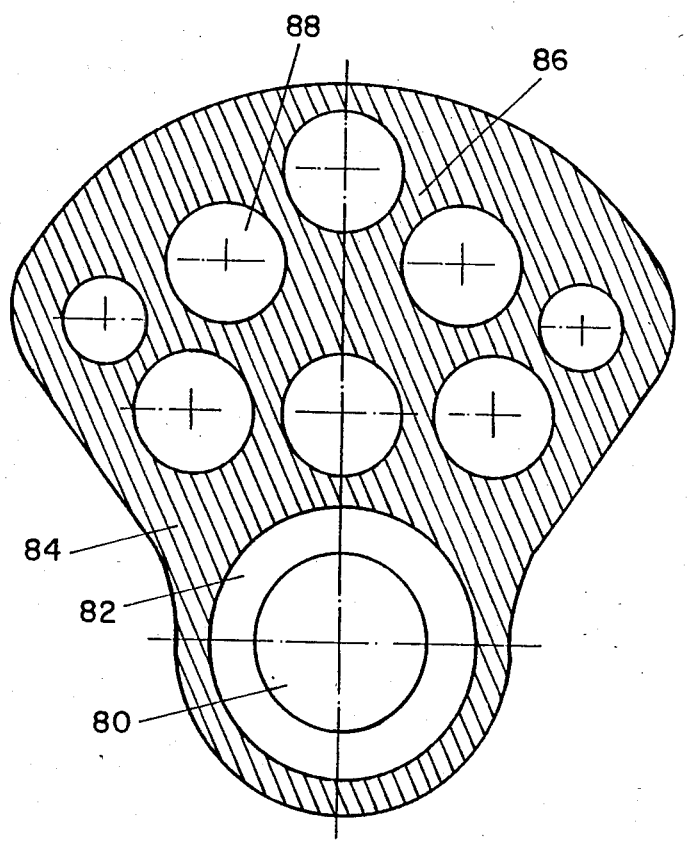

FIG. 5 illustrates an alternative probe configuration wherein an antenna 80 is located in a bore 82 disposed in a narrowed location in a housing 84. A cooling conduit system 86 includes conduits 88 located peripherally of the antenna on all sides. The embodiment of FIG. 5 is essentially similar to that of FIG. 3 except that the cooling conduits do not entirely surround the antenna in the embodiment of FIG. 5.

Figure 6:
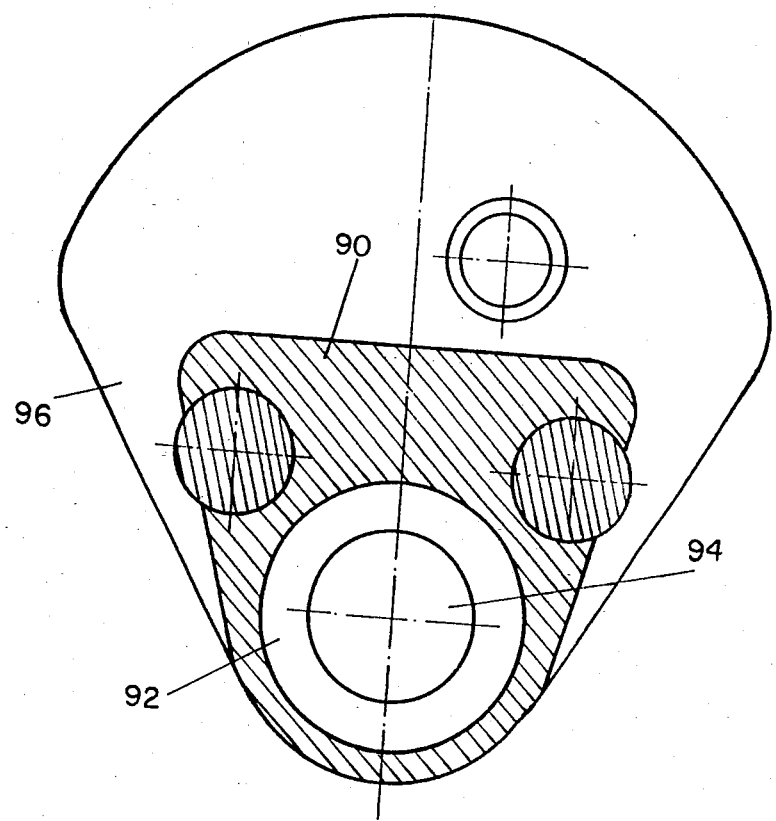

FIG. 6 illustrates yet another configuration of a probe. This configuration employs a probe housing 90 of relatively small cross sectional dimensions, typically 20 mm. Disposed in a bore 92 in housing 90 is an antenna 94. Substantially surrounding housing 90 is a flexible envelope 96 which is coupled to a source of circulating cooling liquid. The embodiment of FIG. 6 has the particular advantage that it may be inserted into a cavity and then rotated at will into a desired position. Only after suitable positioning is the envelope 96 inflated with coolant to fill the cavity according to the anatomical configuration of the cavity and the tumor.

Figure 7:
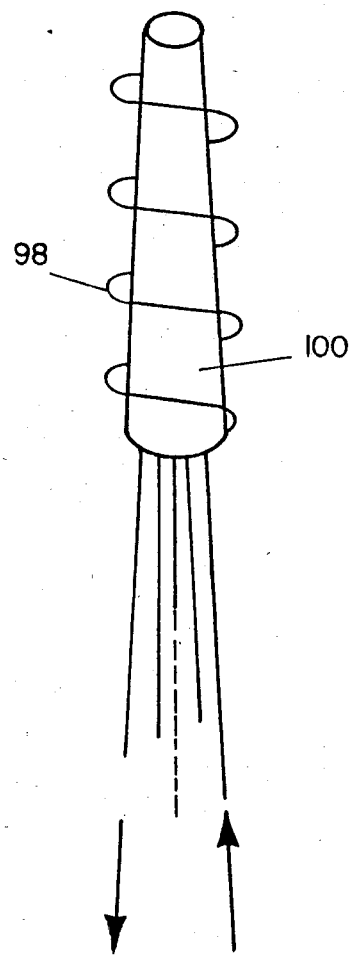
FIG. 7 is a pictorial illustration of an alternative configuration of probe constructed and operative in accordance with an embodiment of the invention.

FIG. 7 is a pictorial illustration of an alternative embodiment of a probe. Here the cooling fluid conduit 98 is provided along the outer surface of the probe housing 100, typically in the form of a helix.

Reference is now made to FIGS. 8A and 8B which illustrate a preferred embodiment of the present invention incorporating an externally disposed coolant circulation conduit as illustrated in FIG. 7. FIG. 8A is a side view illustration of a probe assembly 101 including a broadened forward section 102, a narrowed intermediate section 104, a handle portion 106 and a coaxial antenna connection 107. FIG. 8B is a cross sectional illustration of the forward section 102.

The probe of FIGS. 8A and 8B comprises a single RF microwave antenna 108, typically a quarter-wave dipole antenna, which is located in a bore 110 formed in forward section 102. The cross section of the forward section 102 is preferably pear shaped, as illustrated in FIG. 8B, and the antenna 108 is disposed in the broader portion thereof. Preferred dimensions of the forward section are as indicated in FIGS. 8A and 8B.

The forward section 102 is typically formed of Teflon and is provided with an additional bore 112 for supply of coolant fluid. Bore 112 terminates in a side outlet 114 which is typically coupled to a flexible conduit 116 having an inner diameter of 2/16th of an inch and an outer diameter of 3/16th of an inch. The flexible conduit 116 is tightly wound about the forward section 102 as illustrated and is kept in place by the provision of a protective sheath 118, typically formed of thin plastic or rubber, which sheath conforms to the ribbed configuration defined by the coils of flexible conduit 116.

Cooling fluid communication to bore 112 and from the outlet of flexible conduct 116 is provided via conduits 120 which extend through handle portion 106 to suitable flexible conduits 122 which are connected to coolant circulation apparatus (not shown).

Alternative embodiments of probe configurations may alternatively be employed. One example is shown in FIG. 9 which illustrates a configuration having a pair of antennas 130.

The particular probe structure illustrated in FIG. 8A has a number of significant advantages:

1. The forward portion 102 is configured so as to be insertable into the rectum forwardly of the sphincter muscle, so as to enable the sphincter muscle, which operates non-voluntarily, to engage the narrowed intermediate 104 and thus prevent inadvertent dislodgement of the probe from the rectum or undesired translation of the probe relative to the tumor, resulting in incorrect aiming of the heat radiation directed thereto.

2. The provision of cooling conduits between the patient's skin and the probe provides enhanced cooling efficiency.

3. The ribbed structure of the cooling conduits provides increased surface area for enhanced cooling efficiency.

4. The ribbed structure of the cooling conduits also provides enhanced engagement between the probe assembly and the body cavity.

5. The use of flexible conduits for the external cooling conduits, enables these conduits to be compressed as they are inserted, for ease of insertion and then to be expanded as a coolant is circulated therethrough for enhanced engagement with the body cavity to prevent inadvertent slippage.

It will be appreciated by persons skilled in the art that the present invention is not limited by what has been particularly shown and described hereinabove. Rather the scope of the invention is defined only by the claims which follow:

I claim:

1. Apparatus for hyperthermic treatment of tumours in the vicinity of the anal body cavity whereby the cavity mucosa and the cavity walls are cooled while simultaneously heating said tumours, said apparatus comprising:

probe means arranged to be insertable into a body cavity and including:

a housing having forward and rearward surfaces;

radiation-producing antenna means rigidly disposed in said housing; and cooling conduit means disposed peripherally of said housing and arranged to receive cooling fluid for cooling body tissue disposed in propinquity thereto, said cooling conduit means comprising flexible conduit coiled about the outside forward peripheral suface of said housing, whereby it may be compressed upon insertion into the anal cavity and expanded forwardly of the sphincter muscle when coolant passes therethrough for secure engagement in said cavity, thus retained by the sphincter muscle.

2. Apparatus according to claim 1 and wherein said coiled conduit defines a ribbed outer surface.

3. Apparatus according to claim 1 and wherein said housing defines a relatively broad cross section forward portion and a narrower intermediate portion, said forward portion having said antenna means defined therein and being surrounded by said cooling conduit means.

4. Apparatus according to claim 1 and wherein said probe means also comprises temperature sensing means.

5. Apparatus according to claim 4 and wherein said temperature sensing means comprise means for sensing the temperature at tissue adjacent said probe means along the radiation path between said antenna means and a tumor.

6. Apparatus according to claim 4 and wherein said temperature sensing means comprise means for sensing the temperature in the vicinity of or inside said tumor.

7. Apparatus according to claim 4 and wherein said temperature sensing means comprise means for sensing the temperature within said cooling conduit means.

8. Apparatus according to claim 4 and also comprising means for governing the power radiated by said antenna means in accordance with the temperature sensed by temperature sensing means.

* * * * *